United States Patent
Langley et al.

(10) Patent No.: US 6,945,963 B2
(45) Date of Patent: Sep. 20, 2005

(54) MEDICAMENT CARTRIDGE

(75) Inventors: Christopher Nigel Langley, Warwickshire (GB); Robert Woolston, Warwick (GB)

(73) Assignee: DCA Design International Limited, Warwick (GB)

(*) Notice: Subject to any disclaimer, the term of this patent is extended or adjusted under 35 U.S.C. 154(b) by 62 days.

(21) Appl. No.: 10/308,011

(22) Filed: Dec. 3, 2002

(65) Prior Publication Data

US 2003/0144634 A1 Jul. 31, 2003

(30) Foreign Application Priority Data

Dec. 6, 2001 (GB) .............................................. 0129184

(51) Int. Cl.[7] .............................. A61M 5/00; A61M 5/32
(52) U.S. Cl. ....................................... 604/232; 604/415
(58) Field of Search .......................... 206/459.1, 459.5, 206/438, 807, 828; 215/45, 201, 216, 247, 316, 317, 321, DIG. 3; 604/87, 88, 207–210, 232, 256, 243, 414, 415

(56) References Cited

U.S. PATENT DOCUMENTS

| 3,150,661 A | 9/1964 | Maki ........................... 604/192 |
| 5,693,027 A | * 12/1997 | Hansen et al. ............... 604/232 |
| 5,989,227 A | 11/1999 | Vetter et al. ................. 604/232 |
| 6,126,646 A | 10/2000 | Hansen et al. ............... 604/256 |

FOREIGN PATENT DOCUMENTS

| CZ | 286 666 B6 | 3/1994 |
| DE | 201 10 690 U1 | 10/2001 |
| FR | 2 714 824 A1 | 7/1995 |
| WO | WO 00 27458 A1 | 5/2000 |
| WO | WO 02 074374 A1 | 9/2002 |

* cited by examiner

*Primary Examiner*—Michael J. Hayes
(74) *Attorney, Agent, or Firm*—Oliff & Berridge, PLC

(57) ABSTRACT

A person having diabetes will often be required to take both slow acting and fast acting forms of insulin. It is important to be able to distinguish readily between medicament cartridges containing different medicaments. The present invention enables a user to distinguish readily between medicament cartridges containing different medicaments. A medicament cartridge and adaptor top assembly is provided, the medicament cartridge comprising a cylinder having a bottleneck provided with a flange at a first end, a fluid impermeable membrane covering the first end, a cap beaded under the flange to retain the fluid impermeable membrane in place, and a piston displaceably located within a second end of the cylinder, and the adaptor top comprising a sleeve having a body portion and a tapered portion, the tapered portion being provided with a smaller diameter end, the smaller diameter end being located beneath the cap.

4 Claims, 1 Drawing Sheet

MEDICAMENT CARTRIDGE

FIELD OF THE INVENTION

The present invention relates to an improved medicament cartridge and, in particular, but not exclusively, to a medicament cartridge for use with a medicament delivery apparatus such as an injection pen or an infuser.

Such medicament delivery apparatus are typically used where a patient or carer is entrusted with a treatment regimen requiring administration of the medicament at regular or semi-regular intervals.

BACKGROUND TO THE INVENTION

Medicament cartridges are produced in large volumes to take advantage of economies of scale. Each of the medicament cartridges in then filled with an appropriate medicament, such as an insulin or human growth hormone.

However it is often the case that a patient will require more than one form of medicament. A person having diabetes will often be required to take both slow acting and fast acting forms of insulin. It is important that a user of the medicament delivery apparatus is able to distinguish readily between medicament cartridges containing different medicaments.

It is an advantage of the present invention that it enables a user to distinguish readily between medicament cartridges containing different medicaments. It is a further advantage that the present invention makes use of known medicament cartridges, thereby enabling economies of scale to be maintained.

SUMMARY OF THE INVENTION

According to a first aspect of the present invention a medicament cartridge and adaptor top assembly comprises a medicament cartridge comprising a cylinder having a bottleneck provided with a flange at a first end, a fluid impermeable membrane covering the first end, a cap beaded under the flange to retain the fluid impermeable membrane in place, and a piston displaceably located within a second end of the cylinder, the adaptor top comprising a sleeve having a body portion and a tapered portion, the tapered portion being provided with a smaller diameter end, the smaller diameter end being located beneath the cap.

The adaptor top may conveniently be provided with information regarding the contents of the medicament cartridge. Preferably, the adaptor top is colour coded to provide the information regarding the contents of the medicament cartridge.

Preferably, the tapered portion comprises a plurality of fingers extending from the body portion. This has the advantage that a medicament cartridge may be inserted 'cap first' through the body portion of the adaptor top the fingers splaying over the cap before closing beneath the cap, thereby proving a quick assembly of the present invention.

BRIEF DESCRIPTION OF THE DRAWINGS

The present invention will now be described, by way of example only, with reference to the accompanying drawings, in which.

DETAILED DESCRIPTION OF THE INVENTION

Figure 1:
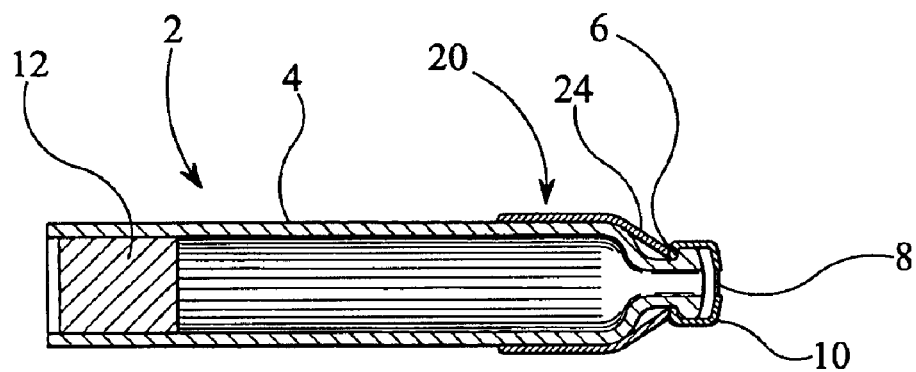
FIG. 1 shows a side section through an assembly in accordance with the present invention.
Figure 2:
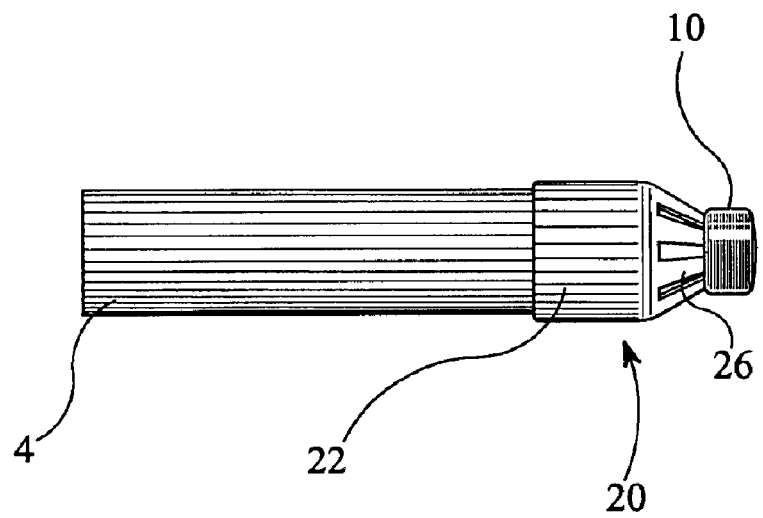
FIG. 2 shows a side view of the assembly of FIG. 1.

Referring to the drawings, there can be seen a medicament cartridge and adaptor top assembly 2 in accordance with the present invention.

The medicament cartridge is of a known type and comprises a cylinder 4 having a bottleneck provided with a flange 6 at a first end. A fluid impermeable membrane 8 covers the first end of the cylinder 4. A cap 10 is beaded under the flange to retain the fluid impermeable membrane 8 in place. A piston 12 is displaceably located within a second end of the cylinder 4.

The adaptor top 20 comprises a sleeve having a body portion 22 and a tapered portion 24. The tapered portion 24 is provided with a smaller diameter end, the smaller diameter end being located beneath the cap 10, that is the smaller diameter end is adjacent the cap 10, such that a portion of the cap 10 is located between the smaller diameter end of the tapered portion 24 and the flange 6.

The adaptor top 20 provides information regarding the contents of the medicament cartridge 2. The adaptor top 20 is conveniently colour coded to provide this information.

In the illustrated embodiment, the tapered portion 24 comprises a plurality of fingers 26 extending from the body portion 22. The adaptor top 20 is preferably formed from a resilient material such as a plastic. This has the advantage that the fingers 26 can flex outwards as required.

In order to put together a medicament cartridge and adaptor top assembly in accordance with the present invention, the medicament cartridge 2 is inserted 'cap first' through the body portion 22 of the adaptor top. The fingers 26 then splay outward allowing passage of the cap 8. The fingers 26 will then close about the bottleneck behind the cap 8. The fingers 26 are sufficiently resilient that further passage of the adaptor top 20 along the medicament cartridge 2 in this direction is prevented.

Since the ends of the fingers 26 remote from the body portion 22 are now located beneath the cap 8, the adaptor top 20 cannot now be removed from the medicament cartridge 2 unless the fingers 26 are removed or damaged in some way. Accordingly, it is a further advantage of the present invention that it provides a tamper evident indication as to the adaptor top 20.

Advantageously, a medicament delivery apparatus with which the medicament cartridge and adaptor top assembly is to be used includes a mating surface for abutment with the adaptor top 20. If the adaptor top 20 does not mate with the mating surface of the medicament delivery apparatus, this provides an indication that the medicament cartridge and adaptor assembly is unsuitable for use with that medicament delivery apparatus.

What is claimed is:

1. A medicament cartridge and adaptor top assembly comprising a medicament cartridge that comprises a cylinder having a bottleneck provided with a flange at a first end, a fluid impermeable membrane covering the first end, a cap beaded under the flange to retain the fluid impermeable membrane in place, a piston displaceably located within a second end of the cylinder and an adaptor top that comprises a sleeve having a body portion and a tapered portion, the tapered portion being provided with a smaller diameter end, the smaller diameter end being located beneath the cap.

2. An assembly according to claim 1, in which the adaptor top is provided with information regarding the contents of the medicament cartridge.

3. An assembly according to claim 2, in which the adaptor top is colour coded to provide the information regarding the contents of the medicament cartridge.

4. An assembly according to claim 1, in which the tapered portion comprises a plurality of fingers extending from the body portion.

* * * * *